United States Patent
Kulprathipanja

(10) Patent No.: US 7,638,677 B2
(45) Date of Patent: Dec. 29, 2009

(54) MIXED MATRIX ADSORBENT FOR PARA-XYLENE SEPARATION

(75) Inventor: Santi Kulprathipanja, Inverness, IL (US)

(73) Assignee: UOP LLC, Des Plaines, IL (US)

(*) Notice: Subject to any disclaimer, the term of this patent is extended or adjusted under 35 U.S.C. 154(b) by 288 days.

(21) Appl. No.: 11/534,264

(22) Filed: Sep. 22, 2006

(65) Prior Publication Data

US 2008/0076952 A1 Mar. 27, 2008

(51) Int. Cl.
*C07C 7/12* (2006.01)

(52) U.S. Cl. .................. 585/828; 585/820; 585/831

(58) Field of Classification Search .......... None
See application file for complete search history.

(56) References Cited

U.S. PATENT DOCUMENTS

| | | | | |
|---|---|---|---|---|
| 2,882,244 A | * | 4/1959 | Milton | 423/718 |
| 2,985,589 A | | 5/1961 | Broughton et al. | 210/34 |
| 3,130,007 A | * | 4/1964 | Breck | 423/711 |
| 3,510,423 A | | 5/1970 | Neuzil et al. | 208/310 |
| 3,686,342 A | | 8/1972 | Neuzil | 260/674 SA |
| 3,734,974 A | | 5/1973 | Neuzil | 260/674 SA |
| 3,878,129 A | * | 4/1975 | Rosback | 423/715 |
| 4,842,836 A | | 6/1989 | Lok et al. | 423/328 |
| 4,965,233 A | | 10/1990 | Speronello | 502/65 |
| 5,107,062 A | | 4/1992 | Zinnen | 585/828 |
| 5,849,981 A | * | 12/1998 | Kulprathipanja | 585/828 |
| 5,900,523 A | | 5/1999 | Kulprathipanja | 585/828 |
| 5,948,950 A | | 9/1999 | Hotier et al. | 585/828 |
| 6,027,548 A | | 2/2000 | Ackley et al. | 95/96 |
| 6,616,899 B1 | | 9/2003 | Upson | 422/139 |
| 6,706,938 B2 | | 3/2004 | Roeseler et al. | 585/820 |
| 6,869,521 B2 | | 3/2005 | Lomas | 208/67 |

* cited by examiner

*Primary Examiner*—Tam M Nguyen
(74) *Attorney, Agent, or Firm*—Arthur E Gooding

(57) ABSTRACT

A process for separating C8 aromatics is disclosed. The process uses at least two adsorbents, and in particular a BaX zeolite and a KY zeolite, for the separation of para-xylene from a mixture of C8 aromatics.

13 Claims, No Drawings

MIXED MATRIX ADSORBENT FOR PARA-XYLENE SEPARATION

FIELD OF THE INVENTION

This invention relates to the field of adsorptive separation. In particular, it is applied to adsorptive separation of para-xylene from other hydrocarbons, and improving the performance of simulated moving bed adsorptive separation processes for the recovery of para-xylene.

BACKGROUND OF THE INVENTION

The separation of various substances through selective adsorption is an important process for producing pure substances. The development of simulated moving bed (SMB) technology, the adsorption separation process can be operated on a continuous basis and for large volumes of materials to be separated and is used in a variety of processes in the petrochemical industry. For simulated moving bed technology, the process uses a multiport rotary valve to redirect flow lines in the process. The simulation of a moving adsorbent bed is described in U.S. Pat. No. 2,985,589 (Broughton et al.). In accomplishing this simulation, it is necessary to connect a feed stream to a series of beds in sequence, first to bed no. 1, then to bed no. 2, and so forth for numerous beds, the number of beds often being between 12 and 24. These beds may be considered to be portions of a single large bed whose movement is simulated. Each time the feed stream destination is changed, it is also necessary to change the destinations (or origins) of at least three other streams, which may be streams entering the beds, such as the feed stream, or leaving the beds. The moving bed simulation may be simply described as dividing the bed into series of fixed beds and moving the points of introducing and withdrawing liquid streams past the series of fixed beds instead of moving the beds past the introduction and withdrawal points. A rotary valve used in the Broughton process may be described as accomplishing the simultaneous interconnection of two separate groups of conduits. There are numerous patents and publications describing the mechanical aspects and internals of the SMB apparatus.

The use of simulated moving beds is important for the separation of xylenes, and especially para-xylene from a mixture of xylenes and other C8 aromatic compounds, such as ethylbenzene. U.S. Pat. No. 3,686,342 issued to R. W. Neuzil describes the separation of para-xylene from a mixture of xylenes using a zeolitic adsorbent and with para-diethylbenzene as the desorbent. This is a good representation of a commercial operation. The SMB process generates a raffinate stream and an extract stream, and the handling of these streams are depicted in U.S. Pat. No. 3,510,423 issued to R. W. Neuzil et al.

Another aspect of the process is the importance of water in the separation performance. U.S. Pat. No. 5,948,950 issued to G. Hotier et al. describes the process and the importance of zeolite hydration to the separation performance. Hydration is maintained by the injection of water into one of the process streams circulating through the adsorbent. The desorbent to feed ration (S/F) disclosed in this reference varies from 0.6 to 2.5. The reference describes the use of several molecular sieve based adsorbents including barium and potassium exchanged X and Y zeolites, but does not suggest the use of a mixture of zeolites for the process. The performance of the process is measured in terms of a performance index designated IP. This reference, like the others cited above, does not discuss the importance of desorbent purity to the process performance.

There are many different process requirements in moving bed simulation processes, resulting in different flow schemes and thus variations in rotary valve arrangement. One process that is important is the production of para-xylene by separation of para-xylene from a hydrocarbon mixture comprising C8 compounds, especially from other xylenes and from ethylbenzene.

There is substantial room for improvement in the SMB process that can improve recovery of para-xylene.

SUMMARY OF THE INVENTION

The invention provides an improved method of separating para-xylene from a feed stream of C8 aromatic compounds. The process involves contacting the feed stream with a mixture of adsorbents comprising of two or more para-xylene selective adsorbents. In one embodiment, the process comprises using two faujasite zeolite adsorbents, where a first adsorbent has a silicon to aluminum atomic ratio of less than 1.5, and a second adsorbent has a silicon to aluminum atomic ratio greater than or equal to 1.5. The process provides for use of the mixture of adsorbents in a separation process such as a simulated moving bed process where each bed in the simulated moving bed comprises the adsorbent mixture.

In a preferred embodiment, the adsorbent mixture comprises a first adsorbent of BaX zeolite in an amount from 50% to 99% by volume, and a second adsorbent of KY zeolite in an amount from 1% to 50% by volume.

Other objects, advantages and applications of the present invention will become apparent to those skilled in the art from the following detailed description.

DETAILED DESCRIPTION OF THE INVENTION

Para-xylene is almost exclusively separated from xylene mixtures using simulated moving bed (SMB) technology. The SMB process is a commercial adsorptive separation process using several adsorption beds and moving the inlet streams and outlet streams between the beds, where a process stream comprising para-xylene is passed through the beds. The adsorption beds comprise an adsorbent for preferentially adsorbing the para-xylene and later desorbing the para-xylene using a desorbent, as the process stream. Currently, the SMB process uses a single adsorbent that has the best characteristics for preferentially adsorbing para-xylene.

It has been found that using a mixture of adsorbents produced an unexpected increase in selectivity and capacity. While the mechanism is not known, the adsorption capacity of para-xylene increased when two adsorbents were used, and the increase was not to a level between the capacities of each adsorbent alone, but to a level greater than either adsorbent. The mixture also produced other advantages, including a reduction in the amount of water necessary for hydration of the zeolites for the separation process.

The process comprises contacting a feed mixture comprising para-xylene with at least two adsorbents, wherein the adsorbents are faujasites. One of adsorbents comprises a silicon to aluminum atomic ratio of less than 1.5 and the second adsorbent has a silicon to aluminum atomic ratio greater than or equal to 1.5. The first adsorbent is known as an X zeolite, and preferably the adsorbent is barium substituted X zeolite, or BaX. The second zeolite is known as a Y zeolite, and preferably the adsorbent is potassium substituted Y zeolite, or KY. With the mixture of the BaX and KY zeolites, the BaX is present in an amount between 50% to 99% by volume and the KY zeolite is present in an amount between 1% to 50% by volume. A preferred amount of KY zeolite is an amount between 2% and 20% by volume, with a more preferred an amount between 6% and 14% by volume. A preferred amount of BaX zeolite is an amount between about 80% and 98% by volume, with a more preferred amount between 86% and 94% by volume. X zeolites are known in the art for use in the separation of para-xylene as described in U.S. Pat. No. 6,706,938 and is incorporated by reference in its entirety. Y-zeolites are known in the art and are described in U.S. Pat. Nos. 4,842,836, 4,965,233, 6,616,899, and 6,869,521 and which are incorporated by reference in their entirety.

The first adsorbent, BaX, is preferred to have been treated with sodium (Na) and potassium (K) to form an NaKBaX zeolite, with the combined total amount of the sodium and potassium between 0.01% and 3% by weight of the zeolite.

In the separation process, the feed mixture moves through a series of adsorbent beds, contacting the feed mixture with each of the beds. The para-xylene in the mixture is preferentially adsorbed onto the adsorbent in the beds. With the present invention, the adsorbents can be combined with both adsorbents mixed during the fabrication of the adsorbents such that adsorbent pellets include both adsorbents, or the adsorbents can be a physical mixture of the adsorbent pellets in each adsorbent bed. In the embodiment that the adsorbents are combined in each pellet, the pellet can have the first adsorbent in the pellet interior and the second adsorbent on the pellet exterior, or the pellet can have the second adsorbent in the pellet interior and the second adsorbent on the pellet exterior. The fabrication of adsorbent pellets is known in the art, as described in U.S. Pat. No. 6,649,802 and is incorporated by reference in its entirety. When the adsorbents are physically mixed, each adsorbent bed will contain the adsorbents as a mixture of the two adsorbents in the desired ratios as described above.

In an alternative arrangement, each adsorbent bed comprises two or more adsorbent sections, wherein the adsorption sections are layered, such that the feed mixture first contacts one of the adsorbents in a first section, and then contacts the other adsorbent in a second section. The sections will be sized to accommodate the first adsorbent and the second adsorbent to the appropriate volume ratios as described above. After passing through the adsorption sections, the feed mixture passes to the next adsorbent bed in the system which is also comprised of layered adsorption sections.

In another alternative, the process comprises a plurality of adsorbent beds, wherein the adsorbent beds are disposed in a sequential manner and alternate the adsorbent in each bed, such that the feed mixture flows over a first bed having the first adsorbent, then flows over a second bed having the second adsorbent, followed by a bed having the first adsorbent, and continuing in an alternating manner for the type of adsorbent.

The beds would be sized according to the appropriate volumes for the adsorbents as described above. Likewise, the process can begin with the second adsorbent and continue in an alternating manner.

When the two adsorbents are used in separate layers, or separate beds, the liquid can flow over the adsorbents in either order, i.e. flow over the BaX adsorbent and then the KY adsorbent, or flow over the KY adsorbent and then the BaK adsorbent.

While this description primarily addresses the recovery of a para-xylene, the operating conditions are therefore cited for performance of an SMB system. It is preferred to operate the adsorption zone at conditions which include a temperature between about 120° C. and 200° C. (249° F. to 392° F.) as this provides better selectivity and capacity. Another important operational variable is the water content of the molecular sieve. This variable is necessary for mass transfer considerations, but there is a tradeoff in that water enhances mass transfer of the para-xylene, but reduces capacity of both the para-xylene and total C8 aromatic capacity. Therefore, a balance must be achieved to optimize the process. As a commercial process operates continuously with the adsorbent confined within the chambers the acknowledged method of operation includes adding water, as required, to the feed stream. The level of hydration of the adsorbent is reported on a volatile free basis or by a measurement referred to as Loss on Ignition (LOI) as described in U.S. Pat. No. 5,900,523. In the LOI test the volatile matter content of the zeolitic adsorbent is determined by the weight difference obtained before and after drying a sample of the adsorbent at 900° C. under an inert gas purge such as nitrogen for a period of time sufficient to achieve a constant weight. Other operating variables include the $L_3$/A ratio and the A/F ratio. The $L_3$/A ratio is the ratio of liquid flow through zone 3 of the SMB system to the rate of simulated circulation of selective pore volume through the process. The A/F is the ratio the rate of simulated circulation of selective pore volume through the process to the volumetric feed rate of the feed mixture. The A/F ratio sets an operating curve, specific to a particular $L_3$ rate. Operating with an A/F ratio of about 0.5 to about 0.7 is preferred. A process unit designed for normally producing a high purity product (e.g. 99%) will operate at the higher end of this general range.

The use of a mixture of adsorbents allows for improving the return on existing para-xylene separation units without replacing the unit, but by changing the adsorbents during a normal reload process when the adsorbents are scheduled to be replaced.

EXAMPLES

Baseline tests were run for comparison with tests involving mixed adsorbents.

TABLE 1

Reference BaX and KY averages for three test runs

| Adsorbent | LOI @ 900° C. | PX Cap (ml) | Tot. Cap. (ml) | PX trans. rate, (sec) | PX half width by pulse test | PX/pDEB | PX/EB | PX/OX | PX/MX |
|---|---|---|---|---|---|---|---|---|---|
| BaX (1) | 5.89 | 3.07 | 10.03 | 547 | 15.75 | 1.46 | 2.35 | 3.94 | 3.52 |
| BaX (2) | 4.86 | 3.5 | 11.13 | 580 | 17.16 | 1.56 | 2.38 | 4.09 | 3.68 |
| BaX (3) | 3.99 | 3.51 | 11.82 | 832 | 18.02 | 1.59 | 2.55 | 2.85 | 3.01 |
| BaX (4) | 2.99 | 3.23 | 11.83 | 868 | 16.5 | 1.68 | 2.51 | 2.55 | 2.75 |
| KY | 1.57 | 2.30 | 10.36 | 220 | 10.65 | 0.74 | 1.90 | 3.45 | 3.68 |

The tests were run in 70 cc columns filled with adsorbent. In Table 1, column 5 is the stage time in seconds by breakthrough. Column 6 is the half width of the paraxylene peak by pulse tests.

Table 1 shows the results for references of test runs showing competitive breakthroughs of para-xylene (PX), ortho-xylene (OX), meta-xylene (MX), ethylbenzene (EB), and desorbant (pDEB) at 177° C. The first BaX series of runs (1) is the reference, and is based upon current commercial considerations, such as water content (LOI) used during the process. The experiments were run to show that it is not apparent that a mixture of two adsorbents would produce a separation greater than with a single adsorbent.

The KY zeolite adsorbent allows for much lower water content, 1.57%, but has a substantially lower para-xylene capacity, and requires much more desorbant that the BaX adsorbents. This is undesirable as it changes the separation profiles during the adsorption and desorption cycles. The water content is important for the operation, and promotes the mass transfer of para-xylene. However, it is desirable to minimize the amount of water. Decreasing the amount of water resulted in increases in the capacity, with a limiting amount of about 4%. Further decreases in the water rapidly deteriorated the mass transfer rate, and adversely affected the adsorbent's capacity for holding para-xylene. This indicates that KY would not be a preferred adsorbent over BaX. However, combining the two adsorbents produced an unexpected increase in adsorption separation over a separation based upon expected separations from any linear combination of the two adsorbents.

A new adsorbent comprising a mixture of two faujasite zeolites provides an increase in capacity of about 10% over the currently uses BaX adsorbent with a similar mass transfer and para-xylene selectivity. This allows for a reduction in the total amount of adsorbent by the addition of an inferior adsorbent to the preferred adsorbent to achieve the same results. This will result in significant savings and increased purity for para-xylene production.

In one experiment, a feed mixture was contacted first with a BaX adsorbent, followed by contacting with a KY adsorbent, and 8% improvement was obtained. It was found that using the two adsorbents in sequence as each stage of the SMB system still resulted in improvements in para-xylene separation.

Example 1

Experiments were run using a mixed matrix adsorbent against a reference BaX adsorbent. The mixed matrix adsorbent (MMA) was a 90/10 mix of BaX and KY zeolites. In order to achieve the same levels of para-xylene purity, and the same levels of recovery, the reference BaX adsorbent required a larger selective pore volume for the same feed rates.

TABLE 2

SMB Performance of BaX vs. MMA at 177° C.

|  | BaX | MMA |
|---|---|---|
| LOI fresh % | 6.05 | 3.89 |
| Cycle time (min) | 34 | 34 |
| Zone III | 2.96 | 2.83 |
| Zone II | 1.45 | 1.49 |
| A/F | 0.63 | 0.58 |
| PX purity, % | 99.2 | 99.2 |
| PX recovery, % | 95 | 95 |
| Improvement |  | 8% over BaX |

In another set of experiments, a mixed matrix adsorbent was compared with a reference adsorbent used for para-xylene separation. For comparison, the reference adsorbent was also run under operating conditions with reduced water content.

TABLE 3

Breakthrough Performance of BaX and MMA

| Adsorbent | LOI | PX cap | Total cap | PX rate | PX by PT | PX/ pDEB | PX/ EB | PX/ OX | PX/ MX | cap increase |
|---|---|---|---|---|---|---|---|---|---|---|
| BaX (ref) | 5.8–6.3 | 3.2 | 10.59 | 502 | 13.93 | 1.42 | 2.17 | 4.03 | 3.74 |  |
| BaX | 3.99 | 3.5 | 11.74 | 832 | 20 | 1.6 | 2.53 | 2.85 | 3 | 9% |
| MMA | 3.89 | 3.47 | 11.58 | 486.7 | 15.7 | 1.54 | 2.5 | 3.27 | 3.28 | 9% |

The LOI is at 900° C., and the capacities are measured in ml per 70 ml adsorbent. The reference was an average of 16 runs, while the MMA and the second BaX were averages of three runs each. The results show that with respect to the reference, the BaX adsorbent with a water content between 5.8 and 6.3%, the capacity increased when the water content was reduced to about 4%. However, there was a significant degradation in the mass transfer rate of the para-xylene, which would ultimately require a much larger bed, or series of beds to obtain good purity. The mixed matrix adsorbent (MMA) however, allowed for a reduced water content in the same range, about 4%, and achieved the same capacity increase while having an improved mass transfer rate of the para-xylene and an increased capacity for para-xylene over the reference. The mixed matrix adsorbent achieved significant improvement without sacrificing performance.

Competitive breakthrough and pulse tests are used to evaluate the performance of an adsorbent. The performance of the MMA is evaluated based upon the ratio of BaX to KY. In addition, tests were run where the LOI was adjusted to the BaX and KY prior to mixing with greater amount of water injected into the BaX adsorbent.

TABLE 4

Mixed Matrix Adsorbent - Competitive Breakthrough of PX, EB, MX, OX, and pDEB at 177° C.

| Adsorbent | LOI @ 900° C. | PX Cap (ml) | Tot. Cap. (ml) | PX trans. rate, (sec) | PX Rate (by pulse test) | PX/pDEB | PX/EB | PX/OX | PX/MX |
|---|---|---|---|---|---|---|---|---|---|
| 50/50 MMA | 2.45 | 2.86 | 10.92 | 551 | 16.61 | 1.14 | 2.22 | 2.88 | 3.07 |
| 86/14 MMA | 3.70 | 3.22 | 11.01 | 543 | 14.50 | 1.35 | 2.46 | 3.46 | 3.43 |
| 86/14 MMA | 4/1.6 | 3.45 | 11.56 | 550 | 14.38 | 1.46 | 2.45 | 3.46 | 3.28 |
| 86/14 MMA | 4/1.6 | 3.36 | 11.25 | 537 | 15.72 | 1.45 | 2.49 | 3.40 | 3.38 |

The results, shown in Table 4 indicate there is high performance for separation of para-xylene from a mixture of C8 aromatics. The mixed adsorbents also provide a good separation with low adsorbent LOI. The reference adsorbent was also operated at a lower hydration, LOI of 3.99%, but as shown in the table, the mass transfer rate climbed from 502 seconds to over 800 seconds. The use of mixed adsorbents provide a significant improvement over an individual adsorbent for the separation process.

While the invention has been described with what are presently considered the preferred embodiments, it is to be understood that the invention is not limited to the disclosed embodiments, but is intended to cover various modifications and equivalent arrangements included with the scope of the appended claims.

What is claimed is:

1. A process for separating para-xylene from a feed mixture comprising:
    contacting the feed mixture with a bed of adsorbent comprising a mixture of at least two adsorbents, a first adsorbent and a second adsorbent, and wherein the first adsorbent comprises a BaX zeolite and the second adsorbent comprises a KY zeolite wherein the amount of KY zeolite is between 2 and 20 percent by volume; and
    recovering the para-xylene from the adsorbents.

2. The process of claim 1 wherein the first adsorbent sodium (Na) and potassium (K) to form a KNaBaX zeolite.

3. The process of claim 2 wherein the total K and Na content is between 0.01% and 3% by weight.

4. The process of claim 1 wherein the amount of KY zeolite is from about 6 to about 14 percent by volume.

5. The process of claim 1 wherein the amount of BaX zeolite is from about 50 to 98 percent by volume.

6. The process of claim 5 wherein the amount of BaX zeolite is from 80 to 94 percent by volume.

7. The process of claim 1 wherein the feed mixture contacts a first adsorption section comprising the first adsorbent, and then contacts a second adsorption section comprising the second adsorbent.

8. The process of claim 1 wherein the feed mixture contacts a bed of adsorbent wherein the adsorbent is a physical mixture of the first adsorbent and the second adsorbent.

9. The process of claim 1 wherein the feed mixture contacts a plurality of adsorbent beds, and wherein the adsorbent beds each comprise one of the first adsorbent and second adsorbent, and wherein there is at least one bed comprising the first adsorbent and at least one bed comprising the second adsorbent.

10. The process of claim 9 wherein the adsorbent beds are arranged in an alternating manner with the first bed comprising one of the first adsorbent and the second adsorbent, and subsequent beds to comprising the other of the first adsorbent and the second adsorbent, such that the feed mixture contacts the adsorbents in an alternating manner.

11. The process of claim 1 wherein the first adsorbent and second adsorbent are fabricated into particles with the first adsorbent in the interior of each particle, and the second adsorbent on the exterior of each particle.

12. The process of claim 1 wherein the first adsorbent and second adsorbent are fabricated into particles with the second adsorbent in the interior of each particle, and the first adsorbent on the exterior of each particle.

13. A process for separating para-xylene from a feed mixture comprising:
    contacting the feed mixture with a bed of adsorbent comprising a mixture of at least two adsorbents, a first adsorbent having a Si to Al ratio of less than 1.5 and a second adsorbent having a Si to Al ratio greater than or equal to 1.5, and wherein the first adsorbent comprises a BaX zeolite and the second adsorbent comprises a KY zeolite wherein the amount of KY zeolite is between 2 and 50 percent by volume; and
    recovering the para-xylene from the adsorbents.

* * * * *